United States Patent [19]

Singh et al.

[11] Patent Number: 5,789,438
[45] Date of Patent: Aug. 4, 1998

[54] INHIBITORS OF FARNESYL-PROTEIN TRANSFERASE

[75] Inventors: Sheo B. Singh, Edison; Russell B. Lingham, Watchung; Keith C. Silverman, Somerset; Deborah L. Zink, Manalapan, all of N.J.; Isabel Martin, Madrid, Spain; Fernando Pelaez, Madrid, Spain; Manuel Sanchez, Madrid, Spain

[73] Assignee: Merck & Co., Inc., Rahway, N.J.

[21] Appl. No.: 924,557

[22] Filed: Sep. 5, 1997

[51] Int. Cl.⁶ .................. A61K 31/365; C07D 493/06
[52] U.S. Cl. .................. 514/453; 549/382; 549/297; 549/384
[58] Field of Search .................. 514/453; 549/382, 549/297

[56] References Cited

U.S. PATENT DOCUMENTS

| | | | |
|---|---|---|---|
| 4,871,727 | 10/1989 | Burg et al. | 514/179 |
| 5,141,851 | 8/1992 | Brown et al. | 435/15 |
| 5,245,061 | 9/1993 | Singh | 560/193 |
| 5,260,465 | 11/1993 | Singh et al. | 562/523 |
| 5,260,479 | 11/1993 | Singh | 560/190 |

OTHER PUBLICATIONS

J. of Biol. Chem., vol. 268, No. 11, pp. 7617–7620 (1993, by J. B. Gibbs, et al.

Science, vol. 260, pp. 1934–1937, (1993), by N. E. Kohl, et al.

Proc. Natl. Acad. Sci. USA, vol. 88, pp. 732–736, Biochemistry (1991), by Y. Reiss, et al.

Carcinogenesis, vol. 15, No. 11, pp. 2649–2652, (1994), by S. Schulz, et al.

Tetrahedron Letters, vol. 35, No. 27, pp. 4693–4696 (1994), by S. B. Singh, et al.

The Terpenes, vol. IV, pp. 39–115 (1991).

Cancer Research, vol. 55, pp. 5302–5309 (1995), by L. Sepp–Lorenzino, et al.

Nature Medicine, vol. 1, No. 8, pp. 792–797 (1995), by N. E. Kohl, et al.

Archives of Biochem. & Piophysics, vol. 300, No. 2, pp. 724–733 (1993), by W. D. Mes, et al.

Steroids, vol. 53/3–5, pp. 579–596 (1989), E. J. Parish, et al.

*Primary Examiner*—Jane Fan
*Attorney, Agent, or Firm*—David A. Muthard; Mark R. Daniel; Elliott Korsen

[57] ABSTRACT

The present invention is directed to steroidal or terpenoidal compounds which inhibit farnesyl-protein transferase (FPTase). The invention is further directed to chemotherapeutic compositions containing the compounds of this invention and methods for inhibiting farnesyl-protein transferase and treatment of cancer.

6 Claims, No Drawings

INHIBITORS OF FARNESYL-PROTEIN TRANSFERASE

BACKGROUND OF THE INVENTION

The Ras protein is part of a signalling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation Ras is induced to exchange GDP for GTP and undergoes a conformational change. The GTP-bound form of Ras propagates the growth stimulatory signal until the signal is terminated by the intrinsic GTPase activity of Ras, which returns the protein to its inactive GDP bound form (D. R. Lowy and D. M. Willumsen, *Ann. Rev. Biochem.* 62:851–891 (1993)). Mutated ras genes are found in many human cancers, including colorectal carcinoma, exocrine pancreatic carcinoma, and myeloid leukemias. The protein products of these genes are defective in their GTPase activity and constitutively transmit a growth stimulatory signal.

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys—Aaa$^1$—Aaa$^2$—Xaa" box (Cys is cysteine, Aaa is an aliphatic amino acid, the Xaa is any amino acid) (Willumsen et al., *Nature* 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. (S. Clarke., *Ann. Rev. Biochem.* 61:355–386 (1992); W. R. Schafer and J. Rine, *Ann. Rev. Genetics* 30:209–237 (1992)). The Ras protein is one of several proteins that are known to undergo post-translational farnesylation. Other farnesylated proteins include the Ras-related GTP-binding proteins such as Rho, fungal mating factors, the nuclear lamins, and the gamma subunit of transducin. James, et al., *J. Biol. Chem.* 269, 14182 (1994) have identified a peroxisome associated protein Pxf which is also farnesylated. James, et al., have also suggested that there are farnesylated proteins of unknown structure and function in addition to those listed above Inhibition of farnesyl-protein transferase has been shown to block the growth of Ras-transformed cells in soft agar and to modify other aspects of their transformed phenotype. It has also been demonstrated that certain inhibitors of farnesyl-protein transferase selectively block the processing of the Ras oncoprotein intracellularly (N. E. Kohl et al., *Science*, 260:1934–1937 (1993) and G. L. James et al., *Science*, 260:1937–1942 (1993). Recently, it has been shown that an inhibitor of farnesyl-protein transferase blocks the growth of ras-dependent tumors in nude mice (N. E. Kohl et al., *Proc. Natl. Acad. Sci U.S.A.*, 91:9141–9145 (1994).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG—CoA reductase, the rate limiting enzyme for the production of polyisoprenoids including farnesyl pyrophosphate. Farnesyl-protein transferase utilizes farnesyl pyrophosphate to covalently modify the Cys thiol group of the Ras CAAX box with a farnesyl group (Reiss et al., *Cell*, 62:81–88 (1990); Schaber et al., *J. Biol. Chem.*, 265:14701–14704 (1990); Schafer et al., *Science*, 249:1133–1139 (1990); Manne et al., *Proc. Natl. Acad. Sci USA*, 87:7541–7545 (1990)). Inhibition of farnesyl pyrophosphate biosynthesis by inhibiting HMG—CoA reductase blocks Ras membrane localization in cultured cells. However, direct inhibition of farnesyl-protein transferase would be more specific and attended by fewer side effects than would occur with the required dose of a general inhibitor of isoprene biosynthesis.

Most of the inhibitors of farnesyl-protein transferase (FPTase) that have been previously described are in two general classes. The first are analogs of farnesyl diphosphate (FPP), while the second class of inhibitors is related to the protein substrates (e.g., Ras) for the enzyme. The peptide derived inhibitors that have been described are generally cysteine containing molecules that are related to the CAAX motif that is the signal for protein prenylation. (Schaber et al., ibid; Reiss et. al., ibid; Reiss et al., *PNAS*, 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., *Science*, 260:1934–1937 (1993); Graham, et al., *J. Med. Chem.*, 37, 725 (1994)).

Several non-peptidyl natural products having farnesyl-protein inhibitory properties have also been described. For example, inhibitors of farnesyl protein transferase which are citrionic acid derivatives have been isolated as fermentation products from a strain of *Chaetomella acutiseta* (U.S. Pat. No. 5,260,465 and EP-547671-A). Synthetic analogs of those compounds have also been described (U.S. Pat. No. U.S. Pat. No. 5,245,061 and 5,260,479). Several other natural product farnesyl-protein transferase inhibitors have recently been described (S. B. Singh et al., *Tetrahedron Letters*, 35:4693–4696 (1994); S. B. Singh et al., *J. Am. Chem Soc.*, 116:11606–11607 (1994)).

Recently, a steroidal analog has been reported that inhibited the farnesylation of a peptide corresponding to the C-terminus of K-Ras protein (S. Schulz and J. W. Nyce, *Carcinogenesis*, 15:1649–1652 (1994)).

It is, therefore, an object of this invention to develop non-peptide compounds which will inhibit farnesyl-protein transferase and the farnesylation of the oncogene protein Ras. It is a further object of this invention to develop chemotherapeutic compositions containing the compounds of this invention, and methods for producing the compounds of this invention.

SUMMARY OF THE INVENTION

The present invention includes natural product compounds, having steroidal or terpenoidal structures, which inhibit farnesyl-protein transferase, chemotherapeutic compositions containing the compounds of this invention, and methods for producing the compounds of this invention.

The compounds of this invention are illustrated by the following formulae:

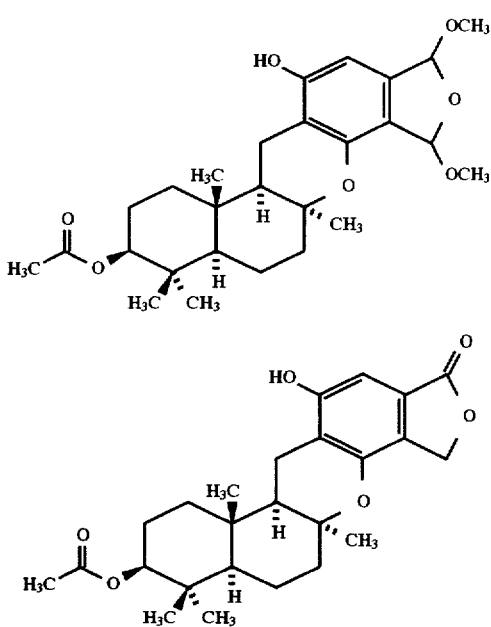

DETAILED DESCRIPTION OF THE INVENTION

The compounds of this invention are useful in the inhibition of farnesyl-protein transferase and are illustrated by the formulae I and II:

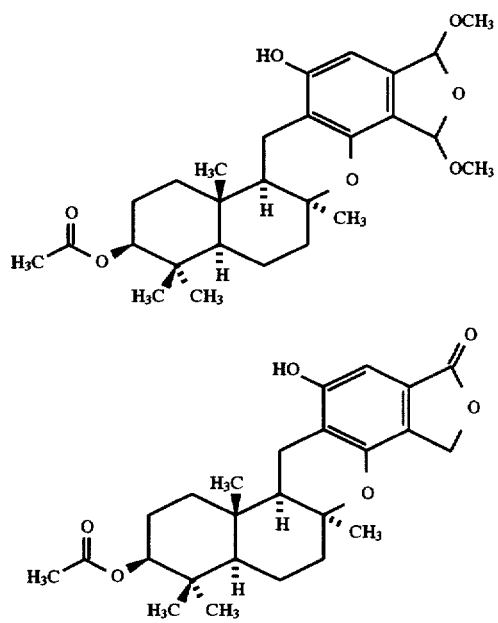

or the pharmaceutically acceptable salts thereof.

The pharmaceutically acceptable salts of the compounds of this invention include the conventional non-toxic salts of the compounds of this invention. For example, such conventional non-toxic salts include those having an alkali metal cation such as sodium or potassium. Other pharmaceutically acceptable cations which form salts may be calcium, magnesium, zinc, ammonium, or alkylammonium cations such as tetramethylammonium, tetrabutylammonium, choline, triethylhydroammonium, meglumine, triethanolhydroammonium, and the like.

Generally, the salts are prepared by reacting the compound of the invention with stoichiometric amounts or with an excess of the desired salt-forming inorganic or organic base in a suitable solvent or various combinations of solvents.

The compounds I and II may be prepared in an aerobic fermentation and isolation procedure employing a novel culture, MF-6199, obtained by culturing the internal tissue of a mushroom identified as *Stachybotrys kampalensis* Hansford. Although the use of this organism is specifically described herein, mutants of the above described organism are also capable of producing the compounds of this invention.

Another novel compound having the formula III is also produced during the fermentation of MF-6199:

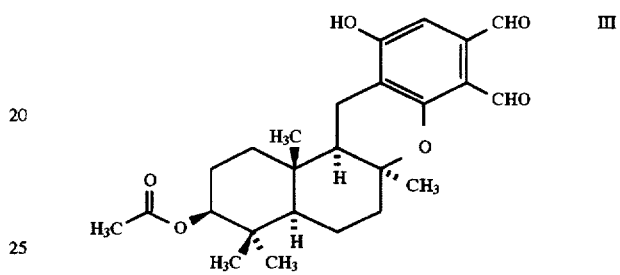

Compound III is the natural product precursor to Compound I, which is produced during the methanolic isolation procedure. Compound I may also be prepared by synthetic manipulation of isolated Compound III.

The culture MF-6199 (F-004,339) was isolated according to the methods of Bills and Polishook (1994) from leaf litter, collected at Bagaces, Palo Verde National Park, Guanacaste Province, Costa Rica. This culture has been deposited with the American Type Culture Collection at 12301 Parklawn Drive, Rockville, Md. 20852 as ATCC 74357.

The following is a general description of culture MF-6199. In the following description, all capitalized color names are from Ridgway (1912). All observations made on colonies grown for 14 days at 25° C. and 67% relative humidity in 12 hr photoperiod:

On oatmeal agar (Difco) colony attaining a diameter of 36 mm. Colony mat velvety, pinkish buff (Light Congo Pink, Vinaceous-Pink, Buff Pink), forming irregular and indistinct concentric circles, sulcate, colony center slightly greenish yellow (Reed Yellow) with a black powdery appearance when sporulating; reverse faint brown; soluble pigment and exudate absent.

On potato-dextrose agar (Difco) colony attaining a diameter of 28 mm. Colony mat woolly, white, sulcate; margin entire, hyaline; exudate few droplets, limited to inoculation point, clear to pinkish; black powdery sporulation occuring at inoculation point; reverse light brown (Chamois, Pinkish Buff); soluble pigment absent.

On MYE (1% malt extract, 0.2% yeast extract (both Difco)) colony attaining a diameter of 32 mm. Colony mat velvety/cottony, white, slightly sulcate at center; reverse light yellow (Warm Buff, Ochraceous-Buff); soluble pigment and exudate absent On cornmeal agar (Difco) colony attaining a diameter of 38 mm. Colony mat hyaline appressed growing submerged; sporulation occurs at colony center as a black, powdery appearance; margin hyaline, entire; reverse, soluble pigment and exudate absent.

Conidiophores simple, erect, 1–3 septate, thick-walled, variable in length up to 150 μm tall, 3–6 μm wide, terminal cell olivaceous, conspicuously roughened, the lower cells hyaline, smooth. Phialides at terminal end in whorls of 4–8, hyaline throughout, obovate to ellipsoid, smooth-walled, 9–12×5–7 µm, with conspicuous collarettes. Conidia aggregated in slimy masses, hyaline when immature, olivaceous to almost black when mature, verrucose, ellipsoidal, 1-celled, 10–14×6–7 µm, biguttulate.

MF-6199 was identified as *Stachybotrys kampalensis* Hansford (Hyphomycetes, Deuteromycotina), a well-known and widespread tropical species. The genus Stachybotrys is characterized by it distinctive inflated phialides and the production of dark conidia in mucilaginous masses. This particular species is distinguished from other *Stachybotrys spp.* by its conidia which are conspicuously roughened, cylindrical-shaped, and of small dimensions (Jong and Davis, 1976).

Literature Cited

1. Bills, G. F. and J. D. Polishook. 1994. Abundance and diversity of microfungi in leaf litter of a lowland rain forest in Costa Rica. Mycologia 86(2) 187–198.

2. Jong, S. C. and E. E. Davis. 1976. Contribution to the knowledge of Stachybotrys and Memnoniella in culture. Mycotaxon 3:409–485.

3. Ridgway, R. 1912. Color standards and color nomenclature. Publ. by the author, Washington, D.C. 43 p. +53 pl.

As used herein, the phrase "active mutant" of a microorganism as described herein is defined as a culture having one or more mutations and which is capable of producing compounds of the formulae II and III. It is well understood in the art that such a mutation may arise spontaneously or may be produced by changing the growth medium of the microorganism or subjecting the microorganism to irradiation or chemical genetic manipulation. It is also understood that one of ordinary skill can determine whether a mutant is "active" based on the Examples herein.

Compounds of this invention can be obtained by culturing the above noted microorganism in aqueous nutrient media containing sources of assimilable carbon and nitrogen, preferably under aerobic conditions, followed by methanolic chromatographic isolation procedures. Nutrient media may also contain mineral salts and defoaming agents.

The preferred sources of carbon in the nutrient medium are carbohydrates such as glucose, glycerin, starch, dextrin, and the like. Other sources which may be included are maltose, mannose, sucrose, and the like. In addition, complex nutrient sources such as oat flour, corn meal, millet, corn and the like may supply utilizable carbon. The exact quantity of the carbon source which is used in the medium will depend, in part, upon the other ingredients in the medium, but is usually found in an amount ranging between 0.5 and 5 percent by weight. These carbon sources can be used individually in a given medium or several sources in combination in the same medium.

The preferred sources of nitrogen are amino acids such as glycine, methionine, proline, threonine and the like, as well as complex sources such as yeast extracts (hydrolysates, autolysates), dried yeast, tomato paste, soybean meal, peptone,casein acid hydrolysate, corn steep liquor, distillers solubles, malt extracts and the like. Inorganic nitrogen sources such as ammonium salts (eg. ammonium nitrate, ammonium sulfate, ammonium phosphate, etc.) can also be used. The various sources of nitrogen can be used alone or in combination in amounts ranging between 0.2 to 20 percent by weight of the medium.

The carbon and nitrogen sources are generally employed in combination, but need not be in pure form. Less pure materials which contain traces of growth factors, vitamins, and mineral nutrients may also be used. Mineral salts may also be added to the medium such as (but not limited to) calcium carbonate, sodium or potassium phosphate, sodium or potassium chloride, magnesium salts, copper salts, cobalt salts and the like. Also included are trace metals such as manganese, iron, molybdenum, zinc, and the like. In addition, if necessary, a defoaming agent such as propylene glycol (P-2000®), polyalkylene glycol, polyethylene glycol or silicone may be added, especially if the culture medium foams seriously.

The preferred process for production of compounds of this invention consists of inoculating spores or mycelia of the producing organism into a suitable medium and then cultivating under aerobic condition.

The fermentation procedure generally is to first inoculate a preserved source of culture into a nutrient seed medium and to obtain, sometimes through a two step process, growth of the organism which serves as seed in the production of the active compounds. After inoculation, the flasks are incubated with agitation at temperature ranging from 20° to 30° C., preferably 25° to 28° C. Agitation rates may range up to 400 rpm, preferably 200 to 220 rpm. Seed flasks are incubated over a period of 2 to 10 days, preferably 2 to 5 days. When growth is plentiful, usually 2 to 5 days, the culture may be used to inoculate production medium flasks. A second stage seed growth may be employed, particularly when going into larger vessels. When this is done, a portion of the culture growth is used to inoculate a second seed flask incubated under similar conditions but employing shorter time.

After inoculation, the fermentation production medium is incubated for 3 to 30 days, preferably 4 to 22 days. The fermentation is conducted aerobically at temperatures ranging from 20° to 40° C. To obtain optimum results, the temperatures are in the range of 22° to 28° C., most preferably 25° to 26° C. The pH of the nutrient medium suitable for producing the active compounds is in the range of 3.5 to 8.5, most preferably 5.0 to 7.5. After the appropriate period for production of the desired compound, fermentation flasks are harvested and the active compound(s) isolated.

An oxygenated solvent, such as an ester or a ketone, or a mixture of an alcoholic solvent and an oxygenated solvent, may be employed to extract a compound(s) of this invention from the fermentation medium.

The mixture is vigorously stirred and filtered, and the filtrate is concentrated under reduced pressure. Water is added to the concentrate and the pH is adjusted to about 3 with a mineral acid. The aqueous concentrate is then repeatedly extracted with a water immiscible oxygenated solvent. The water immiscible organic layer is removed and evaporated to dryness. The residue is then generally subjected to several separation steps such as adsorption and partition chromatography, and precipitation. For each separation step, fractions are collected and combined based on results from an assay and/or HPLC/TLC analysis.

The preferred solvent for extraction of the solid fermentation is methylethylketone. After concentrating the initial extract, the preferred solvent is methanol or ethyl acetate.

The chromatographic separations may be carried out by employing conventional column chromatography with ionic or nonionic absorbents or resins. Silica gel and resins, such as a cellulose-based resin (Sephadex) or Zorbax, are the preferred adsorbents. When silica gel is the adsorbent, an alcohol/chlorohydrocarbon/organic acid mixture such as methanol/chloroform/acetic acid/ water is useful as an eluant. For reverse phase chromatography, the preferred adsorbent is a C8 bonded phase silica gel. The preferred eluant for reverse phase chromatography is a mixture of acetonitrile and water buffered at a low pH, such as 0.1% phosphoric acid, or trifluoroacetic acid. Ionic resins such as Dowex-1 (Cl$^-$) or Dowex-50 (Ca$^{++}$) are also useful in the purification.

The instant compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, myeloid leukemias and neurological tumors. Such tumors may arise by mutations in the ras genes themselves, mutations in the proteins that can regulate Ras activity (i.e., neurofibromin (NF-1), neu, scr, abl, lck, fyn) or by other mechanisms.

The compounds of the instant invention inhibit farnesyl-protein transferase and the farnesylation of the oncogene protein Ras. The instant compounds may also inhibit tumor angiogenesis, thereby affecting the growth of tumors (J. Rak et al. *Cancer Research*, 55:4575–4580 (1995)). Such anti-angiogenesis properties of the instant compounds may also be useful in the treatment of certain forms of blindness related to retinal vascularization.

The compounds of this invention are also useful for inhibiting other proliferative diseases, both benign and malignant, wherein Ras proteins are aberrantly activated as a result of oncogenic mutation in other genes (i.e., the Ras gene itself is not activated by mutation to an oncogenic form) with said inhibition being accomplished by the administration of an effective amount of the compounds of the invention to a mammal in need of such treatment. For example, a component of NF-1 is a benign proliferative disorder.

The instant compounds may also be useful in the treatment of certain viral infections, in particular in the treatment of hepatitis delta and related viruses (J. S. Glenn et al. *Science*, 256:1331–1333 (1992).

The compounds of the instant invention are also useful in the prevention of restenosis after percutaneous transluminal coronary angioplasty by inhibiting neointimal formation (C. Indolfi et al. *Nature medicine*, 1:541–545(1995).

The instant compounds may also be useful in the treatment and prevention of polycystic kidney disease (D. L. Schaffner et al. *American Journal of Pathology*, 142:1051–1060 (1993) and B. Cowley, Jr. et al. *FASEB Journal*, 2:A3160 (1988)).

The instant compounds may also be useful for the treatment of fungal infections.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 20 mg/kg of body weight per day, preferably of between 0.5 mg/kg of body weight to about 10 mg/kg of body weight per day.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immunological, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLES

Examples provided are intended to assist in a further understanding of the invention. Particular materials employed, species and conditions are intended to be further illustrative of the invention and not limitative of the reasonable scope thereof.

Example 1
Preparation of Compound I-IV by Fermentation of MF-6199
Culturing MF-6199

The indetermined hyphomycete culture was maintained in sterile soil and stored at 4° C. until ready for use. The seed cultures were inoculated by aseptically transferring a small amount of the preserved soil into a 250 ml Erlenmeyer flask containing 50 mls of seed medium of the following composition (in g/liter); corn steep liquor, 5.0; tomato paste, 40.0; oat flour, 10.0; glucose, 10.0; and trace elements solution, 10 mls/liter (consisting of, in g/liter: $FeSO_4 \cdot 7H_2O$, 1.0; $MnSO_4 \cdot 4H_2O$, 1.0; $CuCl_2 \cdot 2H_2O$, 0.025; $CaCl_2 \cdot 2H_2O$, 0.1.; $H_3BO_3$, 0.056; $(NH_4)_6MoO_{24} \cdot 4H_2O$ 0.019; $ZnSO_4 \cdot 7H_2O$, 0.2; dissolved in 0.6N HCl). Seed medium was prepared with distilled water, the pH was adjusted to 6.8 by adding NaOH and the medium dispensed into 250 ml Erlenmeyer flasks and capped with cellulose plugs before being autoclaved at 121° C. for 20 minutes. The seed culture was incubated at 25° C., on a gyrotory inoculation of fermentation flasks.

Fermentations were performed on solid substrate production medium formulated as follows: brown rice 10.0 g/250 mls Erlenmeyer flask to which was added 20 mls medium of the following composition prepared with distilled water, (in g/liter) 1.0 g yeast, 0.5 g sodium tartrate and 0.5 g $KH_2PO_4$. Solid substrate production flasks were capped with cellulose plugs and sterilized at 121° C. for 15 minutes. Immediately prior to inoculation, 15.0 mls of distilled water was added to each flask, and the flasks were resterilized at 121° C. for 20 minutes. Each production flask was inoculated with 2.0 mls of vegetative seed growth mixed throughout the solid substrate. Production flasks were incubated without agitation at 25° C. for 28 days. Individual flasks were extracted with 50 mls MEK (methyl ethyl ketone), shaken for 30 minutes and the organic extracts were then pooled.

Example 2
Isolation of Compounds I and II

The solid fermentation product from Example 1 was extracted with methylethylketone, filtered and evaporated to produce an oily residue (600 mg). The residue was dissolved in aqueous methanol and partitioned between hexane, methylene chloride and ethyl acetate. The partition of the compounds having inhibitory activity against farnesyl-protein transferase was monitored by submitting aliquots of the extract or chromatography fraction to the in vitro assay described below in Example 3. All of the activity was concentrated in methylene chloride and ethyl acetate extract. These two extracts were combined and the solvent removed to provide 150 mg solid which was chromatographed on a Sephadex LH-20 in methanol. The activity was eluted after one column volume and was concentrated in two fractions. These two fractions were combined and were chromatographed on a prep Zorbax RX C-8 (22×250 mm) column using acetonitrile-water, step gradient from 45% to 80% acetonitrile at a flow rate of 10 ml/min to give Compound I (56–58 min, 4.4 mg) and Compound II (62–66 min, 2.6 mg) both as an amorphous powder. The structures of Compound I and Compound II were elucidated based on the extensive NMR and mass spectral results.

Isolation of Compound III

A larger batch (2.0 L) of the solid fermentation product from Example 1 was extracted with methylethylketone, filtered and evaporated to produce a yellowish oily residue (30 g). The residue was triturated with hexane and filtered. The residue was thoroughly washed with hexane to give 20 g of buff colored solid (fraction A). 200 mg of this solid in 1.5 mL acetone was chromatographed on a Dynamax C-18 (22×250 mm) HPLC column and eluted with a gradient of aqueous acetonitrile. Gradient was started with 30% acetonitrile for 10 minutes and then ramped to 80% over 50 minutes at a flow rate of 8 mL/min. Lyophilization of the fractions eluting from 50 to 58 minutes gave amorphous powder of compound III. The structure of this, some what less stable, compound was elucidated by NMR and mass spectral studies.

Example 3
Preparation and isolation of Compound IV

To a cooled (0° C.) solution of fraction A (500 mg) was added 20 mL of a 9:1 mixture of methanol-water followed by sodium borohydride (1.0 g). The reaction mixture was stirred at 0° C. for 1 hr, quenched with 5 mL each of acetone and acetic acid and poured on to 400 mL ethyl acetate. The ethyl acetate extract was sequentially washed with 200 mL each of water, 10% aqueous citric acid, water, and 10% aqueous sodium bicarbonate solution. The organic layer was dried over sodium sulfate, concentrated to dryness under reduced pressure and chromatographed over a silica gel column and eluted with 30% acetone in hexane to give 70 mg of semi pure compound IV as an amorphous powder. This was further purified on Dynamax C-18 HPLC column as described for compound III using a 25% to 70% aqueous acetonitrile gradient at a flow rate of 8 mL/min. Lyophilization of the fractions eluted from 46 to 52 minutes gave an colorless powder that was crystallized from acetone-hexane to afford colorless granules.

Physical properties of Compounds I-IV

Compound I: The electron impact mass spectra gave a molecular ion at m/z 474.2601 analyzed for a molecular formula of $C_{27}H_{38}O_7$ (calcd. for 474.2617). The major fragment were observed at m/z 443, 428, and 193. IR: $v_{max}$ (ZnSe): 3346, 2948, 1733, 1690, 1615, 1456, 1370, 1246, 1067, 1033, 1005, 897, 733 cm$^{-1}$; $[\alpha]_{578}^{25}$ −25° (c.0.008, $CH_3OH$).

Compound II: The electron impact mass spectra gave a molecular ion at m/z 428.2206 analyzed for a molecular formula of $C_{25}H_{32}O_6$ (calcd. for 428.2199). The major fragment were observed at m/z 230, and 189. UV: λmax ($CH_3OH$): 223 (ε=13330), 262(ε=5118), 308 (ε=2408); IR: $v_{max}$ (ZnSe): 3369, 2948, 1745, 1735, 1680, 1620, 1470, 1343, 1245, 1168, 1136, 1080, 1015, 936, 915, 773, 737 cm$^{-1}$; $[\alpha]_D^{25}$-11.54 (c, 0.26, $CH_3OH$); mp. turns brown at 180° C. and then melts at 260° C. with decomposition.

Compound III: The electron impact mass spectra gave a molecular ion at m/z 428.2224 analyzed for a molecular formula of $C_{25}H_{32}O_6$ (calcd. for 428.2199). The major fragment were observed at m/z 412, 352, 201, 189, 163, 152 and 119. UV: $\lambda_{max}$ ($CH_3CN$): 208 (β=23369), 230 (sh), 282 (ε=7480), 314 (ε=3360); IR: $v_{max}$(ZnSe): 3317, 2948, 1733, 1651, 1594, 1427, 1368, 1316, 1246, 1167, 1137, 1085, 1026 cm$^{-1}$.

Compound IV: The electron impact mass spectra gave a molecular ion at m/z 432.2558 analyzed for a molecular formula of $C_{25}H_{36}O_6$ (calcd. for 428.2512). The major fragment were observed at m/z 414, 354, 205, 189, 165, and 148. UV: $\lambda_{max}$ (CH$_3$CN): 214 ($\epsilon$=24495), 230 (sh), 285 ($\epsilon$=1565); IR: $\nu_{max}$ (ZnSe): 3400, 3285, 2943, 1733, 1598, 1443, 1352, 1259, 1166, 1136, 1088, 1036, 1017, 999, 973 cm$^{-1}$; mp >290° C. (dec).; $|\alpha|_D^{22}$-66.6° (c,0.45, CH$_3$CN).

TABLE 1

NMR Assignments of Compound I and Compound II in CD$_2$Cl$_2$.

| Position | Compound I ($\delta$C) | Compound I ($\delta$H) | Compound II ($\delta$C) | Compound II ($\delta$H) |
|---|---|---|---|---|
| 1 | 37.8 | 1.10, m | 38.1 | 1.19, m |
|   |      | 1.90, m |      | 1.90, m |
| 2 | 23.7 | 1.53, m | 23.7 | 1.56, m |
|   |      | 1.53, m |      | 1.66, m |
| 3 | 80.8 | 4.47, dd, 11.2, 4.8 | 80.8 | 4.47, dd, 11.8, 4.8 |
| 4 | 37.9 | — | 38.0 | — |
| 5 | 54.6 | 1.05, m | 54.4 | 1.05, m |
| 6 | 18.2 | 1.50, m | 18.1 | 1.50, m |
|   |      | 1.65, m |      | 1.60, m |
| 7 | 40.6 | 1.53, m | 40.4 | 1.62, m |
|   |      | 2.19, brd, 13.6 |  | 2.2, brd, 11.6 |
| 8 | 76.0 | — | 76.8 | — |
| 9 | 48.5 | 1.45, brd, 7.4 | 48.7 | 1.49, brd, 7.6 |
| 10 | 38.3 | — | 38.4 | — |
| 11 | 17.9 | 2.65, dd, 18, 7.2 2.72, d, 18 | 18.5 | 2.73, dd, 19.6, 7.6 2.84, d, 20 |
| 12 | 26.7 | 1.17, s | 27.1 | 1.19, s |
| 13 | 28.4 | 0.90, s | 28.5 | 0.91, s |
| 14 | 16.8 | 0.86, s | 16.9 | 0.86, s |
| 15 | 14.1 | 0.70, s | 14.3 | 0.70, s |
| 1' | 111.2 | — | 117.1 | — |
| 2' | 155.6 | — | 155.3 | — |
| 3' | 100.2 | 6.31, s | 101.4 | 6.80, s |
| 4' | 139.0 | — | 124.9 | — |
| 5' | 118.1 | — | 127.7 | — |
| 6' | 151.6 | — | 150.6 | — |
| 7' | 105.6 | 5.77, s | 171.7 | — |
| 8' | 104.6 | 6.05, s | 68.4 | 5.14, abq, 16 |
| Acetate-CO | 171.1 | — | 171.1 | — |
| Acetate-CH$_3$ | 21.3 | 2.01, s | 21.4 | 2.01, s |
| 7'-OCH$_3$ | 55.2 | 3.47, s | — | — |
| 8'-OCH$_3$ | 52.5 | 3.2, s | — | — |

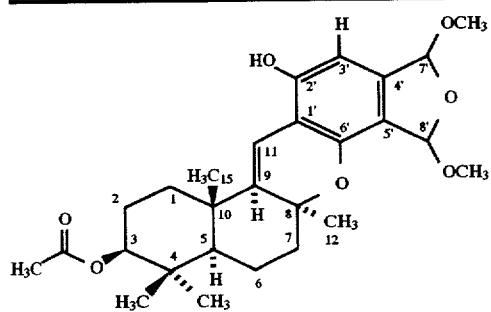

Compound I

TABLE 2

NMR Assignments of Compound III and Compound IV in Acetone-d$_6$.

| Position | Compound III ($\delta$H) | Compound IV ($\delta$C) | Compound IV ($\delta$H) |
|---|---|---|---|
| 1 | 1.10, m | 39.01 | 1.18, m |
|   | 1.90, m |       | 1.90, m |
| 2 | 1.62, m | 27.74 | 1.60, m |
|   | 1.62, m |       | 1.60, m |
| 3 | 4.48, dd, 9.0, 7.2 | 81.48 | 4.48, dd, 9.2, 7.2 |
| 4 | — | 38.86 | — |
| 5 | 1.05, m | 55.36 | 1.15, m |
| 6 | 1.75, m | 19.09 | 1.50, m |
|   | 1.75, m |       | 1.60, m |
| 7 | 1.53, m | 41.67 | 1.60, m |
|   | 2.25, m |       | 2.20, m |
| 8 | — | 76.23 | — |
| 9 | 1.60, m | 49.45 | 1.50, brd, 8 |
| 10 | — | 39.25 | — |
| 11 | 2.70, dd, 18, 8.4 | 19.13 | 2.76, dd, 18, 8 |
|    | 2.80, d, 18 |       | 2.80, d, 18 |
| 12 | 1.28, s | 27.65 | 1.17, s |
| 13 | 0.92, s | 29.22 | 0.91, s |
| 14 | 0.88, s | 17.71 | 0.87, s |
| 15 | 0.79, s | 13.20 | 0.75, s |
| 1' | — | 110.10 | — |
| 2' | — | 155.22 | — |
| 3' | 6.79, s | 107.94 | 6.47, s |
| 4' | — | 141.60 | — |
| 5' | — | 120.44 | — |
| 6' | — | 154.76 | — |
| 7' | 10.41, s | 64.26 | 4.65, brd, 4.4 |
| 8' | 10.41, s | 56.00 | 4.57, brd, 3.0 |
| Acetate-CO | — | 171.17 | — |
| Acetate-CH$_3$ | 2.05, s | 21.55 | 2.00, s |
| 2'-OH |  |  | 8.16, brs |
| 7'-OH |  |  | 3.66, brt, 4.0 |
| 8'-OH |  |  | 4.21, brs |

TABLE 2-continued

NMR Assignments of Compound III and Compound IV in Acetone-d6.

| Position | Compound III (δH) | Compound IV (δC) | Compound IV (δH) |
|---|---|---|---|

Compound III

Compound IV

Example 4
Conversion of Compound III to Compound I:

Fraction A (800 mg), which was devoid of compound I (by HPLC and TLC), was dissolved in 2 mL methylene chloride and was stirred overnight with Sephadex LH-20 (50 mL) in 300 mL methanol containing 2 drops of TFA. The progress of the reaction was monitored by TLC (hexane-ethyl acetate, 1:1). A small amount of compound I was formed after most of the dialdehyde III was consumed. Sephadex LH-20 was removed by filtration and the filtrate was concentrated under reduced pressure to give a gum. One tenth (80 mg) of the resultant gum was chromatographed on a Zorbax RX C-8 (22×250 mm) column. The compounds were eluted, at a flow rate of 8 mL per min, with a successive gradient of 30% to 40% aqueous acetonitrile over 10 min, to 60% over 50 min, to 80% over 20 min. Fractions eluting between 72–74 mm were combined and lyophilized to give mostly compound I. The identity of this compound was verified by comparison of $^1$H NMR spectrum and HPLC.

Example 5
In vitro inhibition of farnesyl-protein transferase

Assays of farnesyl-protein transferase. Partially purified bovine FPTase and Ras peptides (Ras-CVLS, Ras-CVIM and RAS-CAIL) were prepared as described by Schaber et al., *J. Biol. Chem.* 265:14701–14704 (1990), Pompliano, et al., *Biochemistry* 31:3800 (1992) and Gibbs et al., *PNAS U.S.A.* 86:6630–6634 (1989), respectively. Bovine FPTase was assayed in a volume of 100 μl containing 100 mM N-(2-hydroxy ethyl) piperazine-N'-(2-ethane sulfonic acid) (HEPES), pH 7.4, 5 mM MgCl$_2$, 5 mM dithiothreitol (DTT), 100 mM [$^3$H]-farnesyl diphosphate ([$^3$H]-FPP; 740 CBq/mmol, New England Nuclear), 650 nM Ras-CVLS and 10 μg/ml FPTase at 31° C. for 60 min. Reactions were initiated with FPTase and stopped with 1 ml of 1.0M HCL in ethanol. Precipitates were collected onto filter-mats using a TomTec Mach II cell harvester, washed with 100% ethanol, dried and counted in an LKB β-plate counter. The assay was linear with respect to both substrates, FPTase levels and time; less than 10% of the [$^3$H]-FPP was utilized during the reaction period. Purified compounds were dissolved in 100% dimethyl sulfoxide (DMSO) and were diluted 20-fold into the assay. Percentage inhibition is measured by the amount of incorporation of farnesyl in the presence of the test compound when compared to the amount of incorporation in the absence of the test compound.

Human FPTase was prepared as described by Omer et al., *Biochemistry* 32:5167–5176 (1993). Human FPTase activity was assayed as described above with the exception that 0.1% (w/v) polyethylene glycol 20,000, 10 μM ZnCl$_2$ and 100 nM Ras-CVIM were added to the reaction mixture. Reactions were performed for 30 min., stopped with 100 μl of 30% (v/v) trichloroacetic acid (TCA) in ethanol and processed as described above for the bovine enzyme.

Compounds I and II of the instant invention were tested for inhibitory activity against human FPTase by the assay described above and were found to have IC$_{50}$ of <20 μM.

Example 6
In vivo Ras farnesylation assay

The cell line used in this assay is a v-ras line derived from either Rat1 or NIH3T3 cells, which expressed viral Ha-ras p21. The assay is performed essentially as described in DeClue, J. E. et al., *Cancer Research* 51:712–717, (1991). Cells in 10 cm dishes at 50–75% confluency are treated with the test compound (final concentration of solvent, methanol or dimethyl sulfoxide, is 0.1%). After 4 hours at 37° C., the cells are labelled in 3 ml methionine-free DMEM supplemeted with 10% regular DMEM, 2% fetal bovine serum and 400 mCi[$^{35}$S]methionine (1000 Ci/mmol). After an additional 20 hours, the cells are lysed in 1 ml lysis buffer (1% NP40/20 mM HEPES, pH 7.5/5 mM MgCl$_2$/1 mM DTT/10 mg/ml aprotinen/2 mg/ml leupeptin/2 mg/ml antipain/0.5 mM PMSF) and the lysates cleared by centrifugation at 100,000×g for 45 min. Aliquots of lysates containing equal numbers of acid-precipitable counts are bought to 1 ml with IP buffer (lysis buffer lacking DTT) and immunoprecipitated with the ras-specific monoclonal antibody Y13-259 (Furth, M. E. et al., *J. Virol.* 43:294–304, (1982)). Following a 2 hour antibody incubation at 4° C., 200 ml of a 25% suspension of protein A-Sepharose coated with rabbit anti rat IgG is added for 45 min. The immunoprecipitates are washed four times with IP buffer (20 mM HEPES, pH 7.5/1 mM EDTA/1 % Triton X-100.0.5% deoxycholate/0.1%/ SDS/0.1M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to farnesylated and nonfarnesylated ras proteins are compared to determine the percent inhibition of farnesyl transfer to protein.

Example 7
In vivo growth inhibition assay

To determine the biological consequences of FPTase inhibition, the effect of the compounds of the instant invention on the anchorage-independent growth of Rat1 cells transformed with either a v-ras, v-raf, or v-mos oncogene is tested. Cells transformed by v-Raf and v-Mos maybe included in the analysis to evaluate the specificity of instant compounds for Ras-induced cell transformation.

Rat 1 cells transformed with either v-ras, v-raf, or v-mos are seeded at a density of 1×10⁴ cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.1% methanol or an appropriate concentration of the instant compound (dissolved in methanol at 1000 times the final concentration used in the assay). The cells are fed twice weekly with 0.5 ml of medium A containing 0.1% methanol or the concentration of the instant compound. Photomicrographs are taken 16 days after the cultures are seeded and comparisons are made.

What is claimed is:

1. A compound which inhibits farnesyl-protein transferase of the formula I:

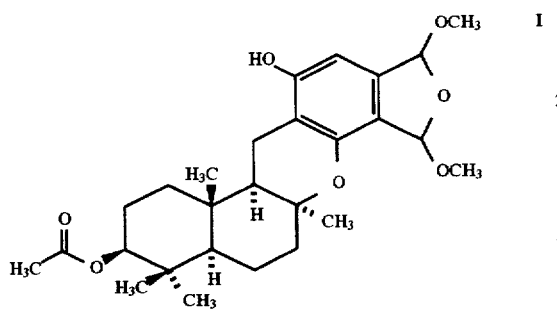

and the pharmaceutically acceptable salts thereof.

2. A compound which inhibits farnesyl-protein transferase of the formula II:

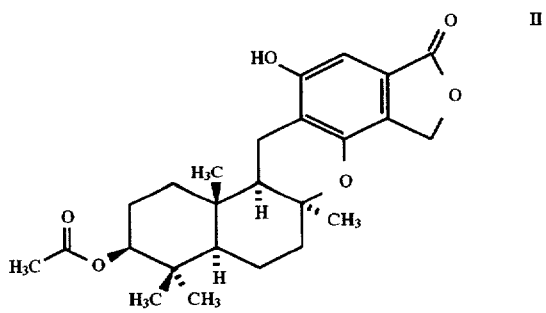

or a pharmaceutically acceptable salt thereof.

3. A pharmaceutical composition comprising a pharmaceutical carrier, and dispersed therein, a therapeutically effective amount of a compound of claim 1.

4. A pharmaceutical composition comprising a pharmaceutical carrier, and dispersed therein, a therapeutically effective amount of a compound of claim 2.

5. A method for treating cancer by inhibiting the farnesylation of an oncogene protein Ras which comprises administering to a mammal in need thereof a therapeutically effective amount of a composition of claim 3.

6. A method for treating cancer by inhibiting the farnesylation of an oncogene protein Ras which comprises administering to a mammal in need thereof a therapeutically effective amount of a composition of claim 4.

* * * * *